United States Patent [19]
Frye et al.

[11] Patent Number: 5,302,589
[45] Date of Patent: Apr. 12, 1994

[54] HETEROCYCLIC INHIBITORS OF 5-ALPHA-TESTOSTERONE REDUCTASE

[75] Inventors: Stephen V. Frye, Durham, N.C.; David Middlemiss, Ware, United Kingdom; Francis G. Fang, Durham, N.C.

[73] Assignee: Glaxo, Inc., Research Triangle Park, N.C.

[21] Appl. No.: 927,091

[22] Filed: Aug. 7, 1992

[51] Int. Cl.$^5$ .......................................... A61K 31/435
[52] U.S. Cl. ........................ 514/210; 514/183; 514/213; 514/218; 514/219; 514/222.2; 514/224.2; 514/224.5; 514/229.5; 514/243; 514/248; 514/253; 514/257; 514/279; 514/280; 514/281; 514/375; 514/410; 540/468; 540/471; 540/476; 540/488; 540/492; 540/576; 544/14; 544/89; 544/99; 544/125; 544/233; 544/245; 544/342; 544/361; 546/14; 546/38; 546/42; 546/77; 548/217; 548/419; 548/420; 549/333
[58] Field of Search ............... 546/42, 38; 540/576, 540/476; 514/210, 213, 253, 279, 280, 224.5; 544/361, 125

[56] References Cited

U.S. PATENT DOCUMENTS 3,138,584 6/1964 Zderic .................................... 540/576

(List continued on next page.)

FOREIGN PATENT DOCUMENTS

004949A1 4/1979 European Pat. Off. .

(List continued on next page.)

OTHER PUBLICATIONS

Diani et al. Jour. Clin. Endoc. vol. 74, pp. 345-350 (1992).

(List continued on next page.)

*Primary Examiner*—Donald G. Daus
*Attorney, Agent, or Firm*—Charles T. Joyner

[57] ABSTRACT

The present invention relates to certain substituted 17 β-substituted carbonyl-6-azaandrost-4-en-3-ones of formula (I):

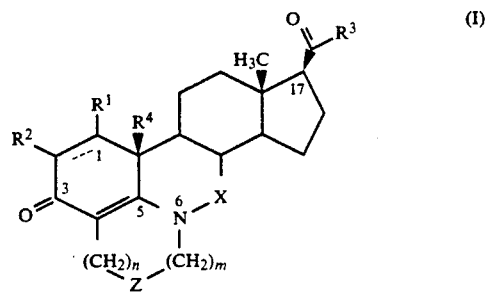

wherein
$R^1$ and $R^2$ are
  i) independently hydrogen or lower alkyl and the bond between the carbons bearing $R^1$ and $R^2$ is a single or a double bond, or
  ii) taken together are a —CH$_2$— group to form a cyclopropane ring, and the bond between the carbons bearing $R^1$ and $R^2$ is a single bond;
X is

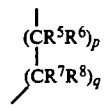

wherein
$R^5$, $R^6$, $R^7$ and $R^8$ are independently hydrogen or lower alkyl,
p and q are independently either 0 or 1;
$R^3$ is lower alkyl, lower alkenyl, lower cycloalkyl, lower alkoxy, thiopyridyl, adamantyl, —NR$^9$R$^{10}$ or —Ar—NR$^9$R$^{10}$
wherein
$R^9$ and $R^{10}$ are
  i) independently, hydrogen or lower alkyl, lower alkenyl, lower alkynyl, lower cycloalkyl, lower alkoxy, adamantyl, aryl, benzyl, diphenylmethyl, norbornyl or
  ii) taken together with the linking nitrogen to form a 4 to 8 atom heterocyclic group,

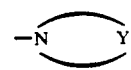

wherein;
Y represents O, CH$_2$, —N=, NH or N(lower alkyl) optionally substituted with one or more lower alkyl groups;
Ar is an aromatic group of 6 to 12 carbons;
$R^4$ is hydrogen or methyl;
Z is —O—, —NH—, —N(lower alkyl), —S—, —SO—, —SO$_2$, —CH$_2$CH$_2$—, —CH=CH—, CO, CO$_2$, O$_2$C, —N=N— —CH=N— or —N=CH—;
n and m are independently 0, 1 or 2;
and pharmaceutically acceptable salts thereof;

their preparation, medical use and pharmaceutical formulations.

5 Claims, No Drawings

U.S. PATENT DOCUMENTS

| | | |
|---|---|---|
| 4,191,759 | 3/1980 | Johnston et al. |
| 4,361,578 | 11/1982 | Alig et al. |
| 4,377,584 | 3/1983 | Rasmusson et al. ............... 546/77 |
| 4,882,319 | 11/1989 | Holt et al. ........................... 540/23 |
| 4,888,336 | 12/1989 | Holt et al. ......................... 514/278 |
| 4,937,237 | 6/1990 | Holt et al. ........................... 514/75 |
| 5,017,568 | 5/1991 | Holt et al. ......................... 514/173 |
| 5,061,801 | 10/1991 | Williams et al. ................... 546/77 |
| 5,061,802 | 10/1991 | Steinberg et al. .................. 546/77 |
| 5,061,803 | 10/1991 | Williams et al. ................... 546/77 |
| 5,098,908 | 3/1992 | Steinberg et al. .................. 540/77 |
| 5,110,939 | 5/1992 | Holt et al. ......................... 548/250 |

FOREIGN PATENT DOCUMENTS

| | | |
|---|---|---|
| 155096A2 | 2/1985 | European Pat. Off. |
| 314199A1 | 2/1985 | European Pat. Off. |
| 200859A1 | 2/1986 | European Pat. Off. |
| 271219A1 | 11/1987 | European Pat. Off. |
| 271220A1 | 11/1987 | European Pat. Off. |
| 277002A2 | 1/1988 | European Pat. Off. |
| 285383A2 | 3/1988 | European Pat. Off. |
| 414490A2 | 8/1990 | European Pat. Off. |
| 414491A2 | 8/1990 | European Pat. Off. |
| 428366A2 | 11/1990 | European Pat. Off. |
| 435321A2 | 12/1990 | European Pat. Off. |
| 462661A2 | 6/1991 | European Pat. Off. |
| 462662A2 | 6/1991 | European Pat. Off. |
| 462664A2 | 6/1991 | European Pat. Off. |
| 462665A2 | 6/1991 | European Pat. Off. |
| 462668A2 | 6/1991 | European Pat. Off. |
| 469547A2 | 7/1991 | European Pat. Off. |
| 469548A2 | 7/1991 | European Pat. Off. |
| 473225A2 | 8/1991 | European Pat. Off. |
| 473226A2 | 8/1991 | European Pat. Off. |
| 478066A2 | 9/1991 | European Pat. Off. |
| 484094A2 | 10/1991 | European Pat. Off. |
| WO91/12261 | 8/1991 | PCT Int'l Appl. |

OTHER PUBLICATIONS

Helliker, Wall St. Jour., Jun. 7, 1991 pp. A1, A7.
Stinson, Chem. & Eng. News, Jun. 7, 1992, pp. 7–8.
Hsia, et al, *J. Invest. Derm.*, 1974, pp. 224–227.
Robaine, et al, *J. Steroid Biochem.*, 8, 1977, pp. 307–310.
Petrow, et al, *Steroids*, 38, 1981, pp. 121–140.
Lian, et al, *J. Steroid Biochem.*, 19, 1983, p. 395.
Holt, et al, *J. Med. Chem.*, 33, 1990, 937–942, "Steroidal A Ring Aryl Carboxylic Acids: A New Class of Steroid 5α–Reductase Inhibitors".
Stoner, et al, *J. Steroid Biochem. Molec. Biol.*, 37, 1990, pp. 375–378.
Brooks, et al, *Steroids*, 47, 1986, pp. 1–19.
Velthuysen, et al, *Tetrahedron Letters*, 27, 1966, 3081–3086, "Synthesis of (±)–N–Methyl–6–aza–8(1–4)–dehydro–19–nor–testosterone".
Speckamp, et al, *Tetrahedron*, 24, 1968, 5893–5898, "The Synthesis of N–Methyl–6–Aza–8(14)–Dehydro–19–Nor–Testosterone".
Kutney, et al, *Candian J. of Chem.*, 41, 1963, 613–619, "Synthesis of 6–Aza Steroids—A Novel Class of Azaandrostane Analogues".
Sampson, et al, *Biochimica et Biophysica Acta*, 960, 1988, 268–274, "The Efects of 6–Azacholest–4–en–3β–ol–7–one, an Inhibitor of Cholesterol 7α–Hydroxylase, on Cholesterol Metabolism and Bile Acid Synthesis in Primary Cultures of Rat Hepatocytes".
Kutney, et al, *Tetrahedron*, 24, 1968, 845–857, "Synthesis of Ring A–Oxygenated 6–Aza Steroids".
Brown, et al, *J. Chem. Soc.*, 1987, 595–599, "The Synthesis of Some Cholesterol Derivatives as Probes for Mechanisms of Cholesterol Metabolism".
Jacobs, et al., 1960, 4033–4039, "The Introduction of Oxyen and Bitrogen into the B Ring of the Steroid Nucleus".
Speckamp, et al, *Tetrahedron*, 24, 1968, 5881–5891, "Synthesis of N–Methyl and N–Ethyl–6–Aza–8(1–4)–Dehydroestrone Methyl Ether".
Hugl, et al, *Tetrahedron*, vol. 29, 1973, 759–767, "Umsetzungen Von $\Delta^5$–Steroidolefinen Mit Pb(OAc)–$4-n(N_3)_n^1$".
Kutney, et al, *Chem. and Ind*, 1961, 1713–1714, "Synthesis of 6–Aza–Steroids: A Novel Class of Steroidal Hormones".
Rasmusson, et al, *J. Med. Chem*, 29, 1986, 2298–2315, "Steroids: Structure–Activity Relationships for Inhibition of 5α–Reductase and Androgen Receptor Binding".
H. Lettré et al., *Liebig's Ann. Chem*, 703, 1967, 147–151, "Verbesserung der Darstellung von 6–Aza–Steroiden".
Rasmusson, et al, *J. Med. Chem.*, 27, 1984, 1690–1701, "Azasteroids as Inhibitors of Rat Prostatic 5α–Reductase".
Imperato–McGinley, et al, *TIG*, 1986, 130–133, "Inherited 5α–Reductase Deficiency in Man".
Jones, et al, *British J. of Urology*, 66, 1990, 506–508, "Origin and Structure of Benign Prostatic Hyperplasia".
Bhattacharya, et al, *Synthetic Communications*, 30(17), 1990, 2683–2690, "Acylimidazolides as Versatile Synthesis Intermediates for the Preparation of Sterically Congested Amides and Ketones: A Practical Synthesis of Proscar ®".

HETEROCYCLIC INHIBITORS OF 5-ALPHA-TESTOSTERONE REDUCTASE

The present invention relates to certain substituted 17β-substituted 6-azaandrost-4-en-3-ones bridged by substituents at the 4 and 6 positions to form a fused, heterocyclic ring system and their use as 5α-testosterone reductase inhibitors.

BACKGROUND OF THE INVENTION

Androgens are responsible for many physiological functions in both males and females. Androgen action is mediated by specific intracellular hormone receptors expressed in androgen responsive cells. Testosterone, the major circulating androgen, is secreted by Leydig cells of the testes under the stimulation of pituitary-derived luteinizing hormone (LH). However, reduction of the 4,5 double bond of testosterone to dihydrotestosterone (DHT) is required in some target tissues, such as prostate and skin, for androgen action. Steroid 5α-reductase in target tissues catalyzes conversion of testosterone to DHT in an NADPH dependent fashion as shown in Scheme A.

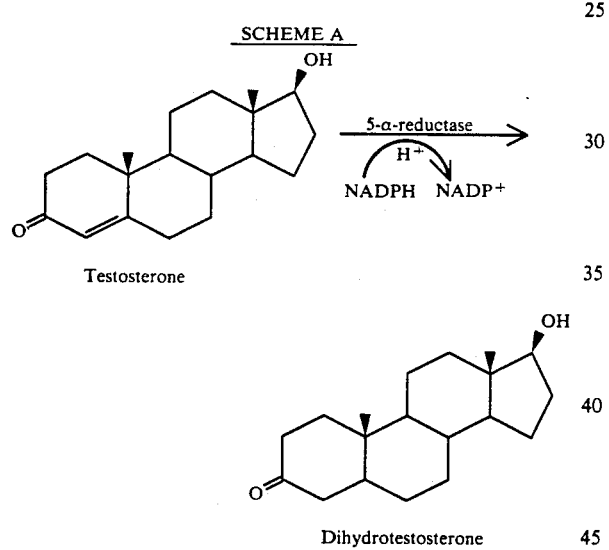

The requirement for DHT to act as an agonist in these target tissues has been highlighted by studies of steroid 5α-reductase deficient individuals who have vestigal prostate glands and do not suffer from acne vulgaris or male pattern baldness (see McGinley, J., et al.,*The New England Journal of Medicine*, 300, No. 22, pp. 1233-37, (1979)). Thus, inhibition of the conversion of testosterone to DHT in these target tissues is anticipated to be useful in the treatment of a variety of androgen responsive diseases, e.g., benign prostatic hypertrophy, prostate cancer, acne, male pattern baldness and hirsutism.

Because of their valuable therapeutic potential, testosterone 5α-reductase inhibitors [hereinafter "5α-reductase inhibitors"] have been the subject of active research worldwide. For example, see: Hsia, S. and Voight, W., J. Invest. Derm., 62, 224 (1973); Robaire, B., et al., J. Steroid Biochem., 8, 307 (1977); Petrow, V., et al., Steroids, 38, 121 (1981); Liang, T., et al., J. Steroid Biochem., 19, 385-390 (1983); Holt, D., J. Med. Chem., 33, 937 (1990); U.S. Pat. Nos. 4,377,584 and 5,017,568. Two particularly promising 5α-reductase inhibitors currently in clinical trials are MK-906 (Merck) and SKF-105657 (SmithKline Beecham), shown in Scheme B.

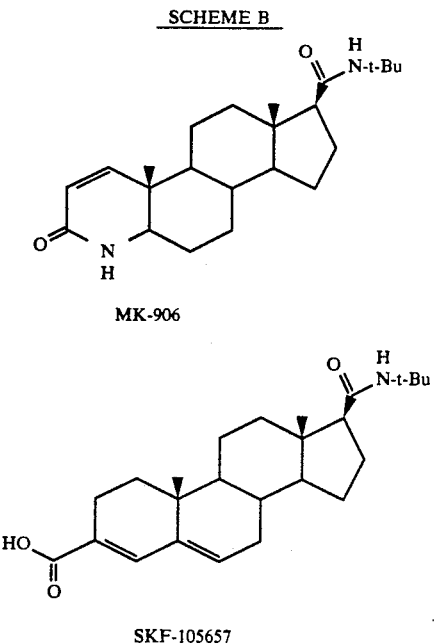

SUMMARY OF THE INVENTION

One aspect of the present invention are the compounds of formula (I),

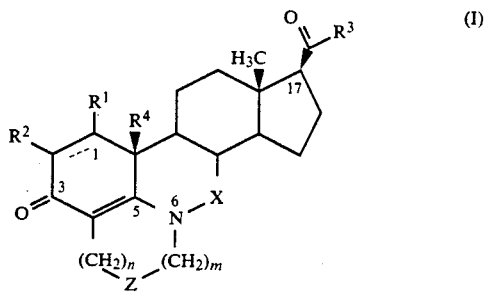

wherein
R$^1$ and R$^2$ are
i) independently hydrogen or lower alkyl and the bond between the carbons bearing R$^1$ and R$^2$ is a single or a double bond, or
ii) taken together are a —CH$_2$— group to form a cyclopropane ring, and the bond between the carbons bearing R$^1$ and R$^2$ is a single bond;
X is

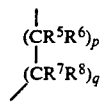

wherein
R$^5$, R$^6$, R$^7$ and R$^8$ are independently hydrogen or lower alkyl,
p and q are independently either 0 or 1;

$R^3$ is lower alkyl, lower alkenyl, lower cycloalkyl, lower alkoxy, thiopyridyl, adamantyl, $-NR^9R^{10}$ or $-Ar-NR^9R^{10}$ wherein $R^9$ and $R^{10}$ are
  i) independently, hydrogen or lower alkyl, lower alkenyl, lower alkynyl, lower cycloalkyl, lower alkoxy, adamantyl, aryl, benzyl, diphenylmethyl, norbornyl or
  ii) taken together with the linking nitrogen form a 4 to 8 atom heterocyclic group of the formula:

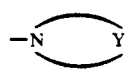

wherein;

Y represents O, $CH_2$, $-N=$, NH or N(lower alkyl) optionally substituted with one or more lower alkyl groups;

Ar is an aromatic group of 6 to 12 carbons;

$R^4$ is hydrogen or methyl;

Z is $-O-$, $-NH-$, $-N(\text{lower alkyl})$, $-S-$, $-SO-$, $-SO_2$, $-CH_2CH_2-$, $-CH=CH-$, CO, $CO_2$, $O_2C$, $-N=N-$ $-CH=N-$ or $-N=CH-$;

n and m are independently 0, 1 or 2;

and pharmaceutically acceptable salts thereof.

A second aspect of the invention is a method of inhibiting testosterone-5α-reductase comprising contacting testosterone-5α-reductase with a compound of formula (I).

Another aspect of the invention is a method of treatment of androgen responsive or mediated disease comprising administering an effective amount of a compound of formula (I) to a patient in need of such treatment.

A further aspect comprises pharmaceutical formulations containing a compound of formula (I) as an active ingredient. Novel chemical intermediates used in the synthesis, as taught herein, of the compounds of formula (I) are also within the scope of the present invention.

DETAILED DESCRIPTION OF THE INVENTION

Compounds

As used herein the term "lower" in reference to alkyl and alkoxy means 1-6 carbons, in reference to alkenyl or alkynyl means 2-6 carbons and in reference to cycloalkyl means 3-6 carbons. The term "aryl" means homocyclic aromatic groups having 6 to 12 carbons, e.g., phenyl and naphthyl. Where $R^9$ and $R^{10}$ are taken together with the linking nitrogen form a 4 to 8 atom heterocyclic group, such groups which may be formed include, but are not limited to, aromatic, unsaturated or saturated rings such as those of 5 or 6 members such as pyrrolidinyl, pyrrolyl, isoxazolyl, imidazolidinyl, pyrazolidinyl, piperidinyl, piperazinyl or morpholinyl, each optionally substituted with one or more lower alkyl groups. Examples of X are $-CH(CH_3)C(C_2H_5)_2-$ and $-C(C_2H_5)_2CHCH_3-$.

Particular groups of compounds of formula (I) are the compounds of formulas (IA), (IB) and (IC)

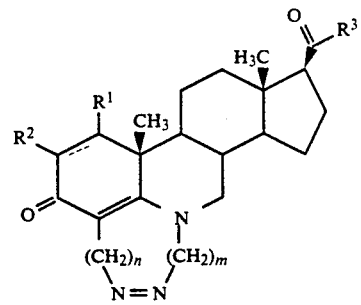

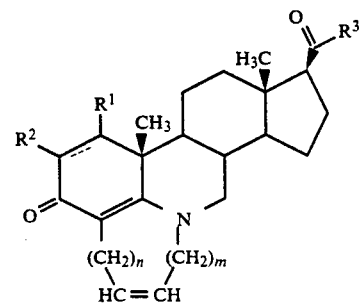

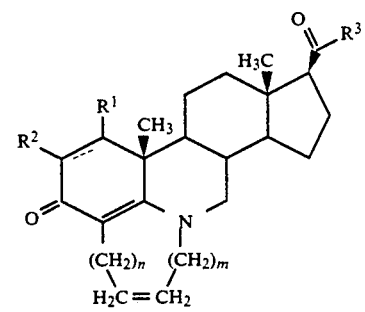

Specific compounds of formula (I) are:

| Compound/Example Number | Compound Name |
| --- | --- |
| 1. | 17β-N,N-Diethylcarbamoyl-6-azaandrost-4,6-diazo-4-en-3-one |
| 2. | 17β-N,N-Diethylcarbamoyl-6-azaandrost-4,6-etheno-4-en-3-one |
| 3. | 17β-N-t-Butylcarbamoyl-6-azaandrost-4,6-etheno-4-en-3-one |
| 4. | 17β-N-t-Butylcarbamoyl-6-azaandrost-4,6-butano-4-en-3-one |

Some of the substituents of the compound of formula (I) may cause asymmetry about the atoms to which they are attached giving rise to either α or β stereochemical configuration. (For a detailed explanation of stereochemical configuration see March, J. *Advanced Organic Chemistry*, 3rd Ed., ch 4, John Wiley & Sons, New York (1985).) Unless otherwise indicated, either the α and β stereo configurations are intended for the substituents.

The compounds of formula (I) can be used in the form of an acid addition salt derived from inorganic or organic acids. Where the salt of a compound of formula (I) is to be used for a human or veterinary medicinal application the salt must be pharmaceutically acceptable. However, non-pharmaceutically acceptable salts of the compounds of formula (I) may be useful as intermediates in the preparation of a corresponding pharmaceutically acceptable salt. Pharmaceutically acceptable salts include, but are not limited to salts with inorganic acids such as hydrochloride, sulfate, phosphate, diphosphate, hydrobromide and nitrate salts or salts with an organic acid such as the acetate, malate, maleate, fumarate, tartrate, succinate, citrate, lactate, methanesulfonate, p-toluenesulfonate, palmoate, salicylate and sterate salts.

Preparation of Compounds

The compounds of the present invention may be prepared by the procedure shown in Scheme I, wherein $R^1$-$R^6$ are as defined for formula (I) and "ΣSiO" is a trisubstituted silyl, such as trialkylsilyl, e.g., triisopropylsilyl, protected hyroxy group:

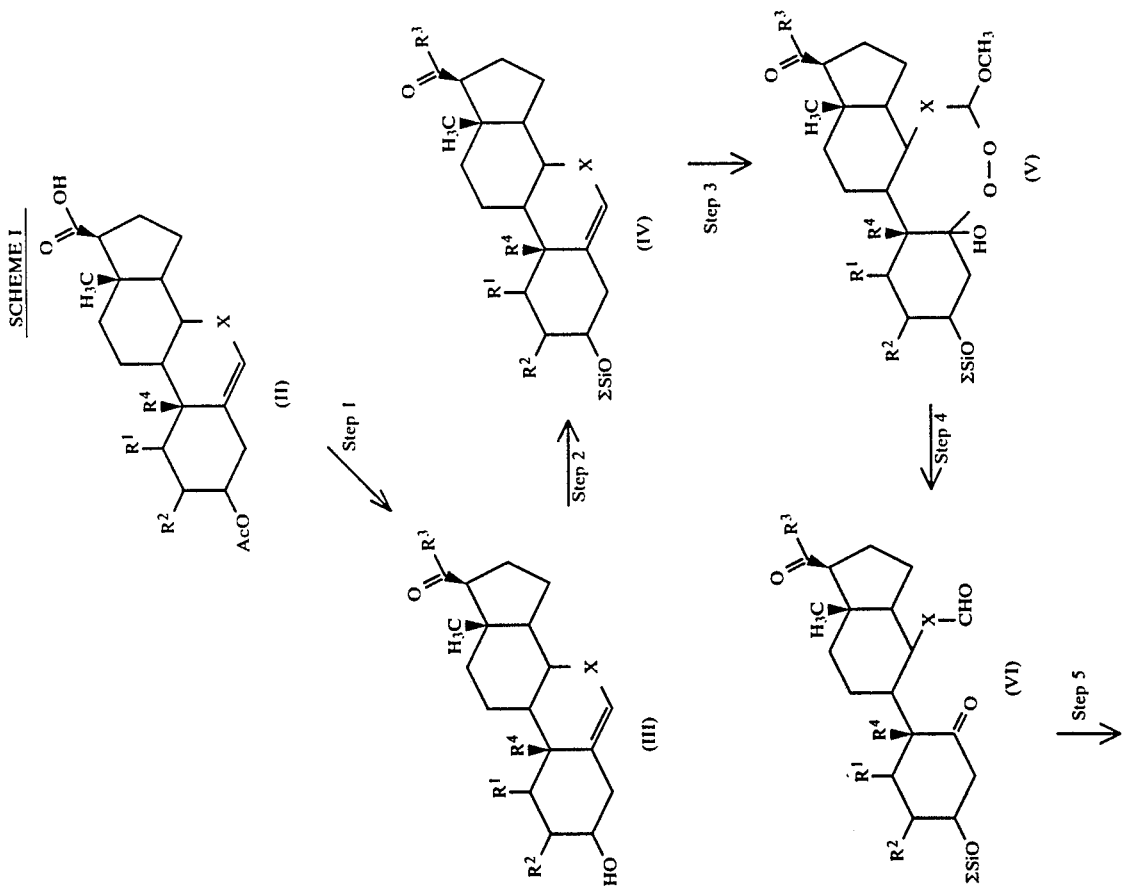
SCHEME I

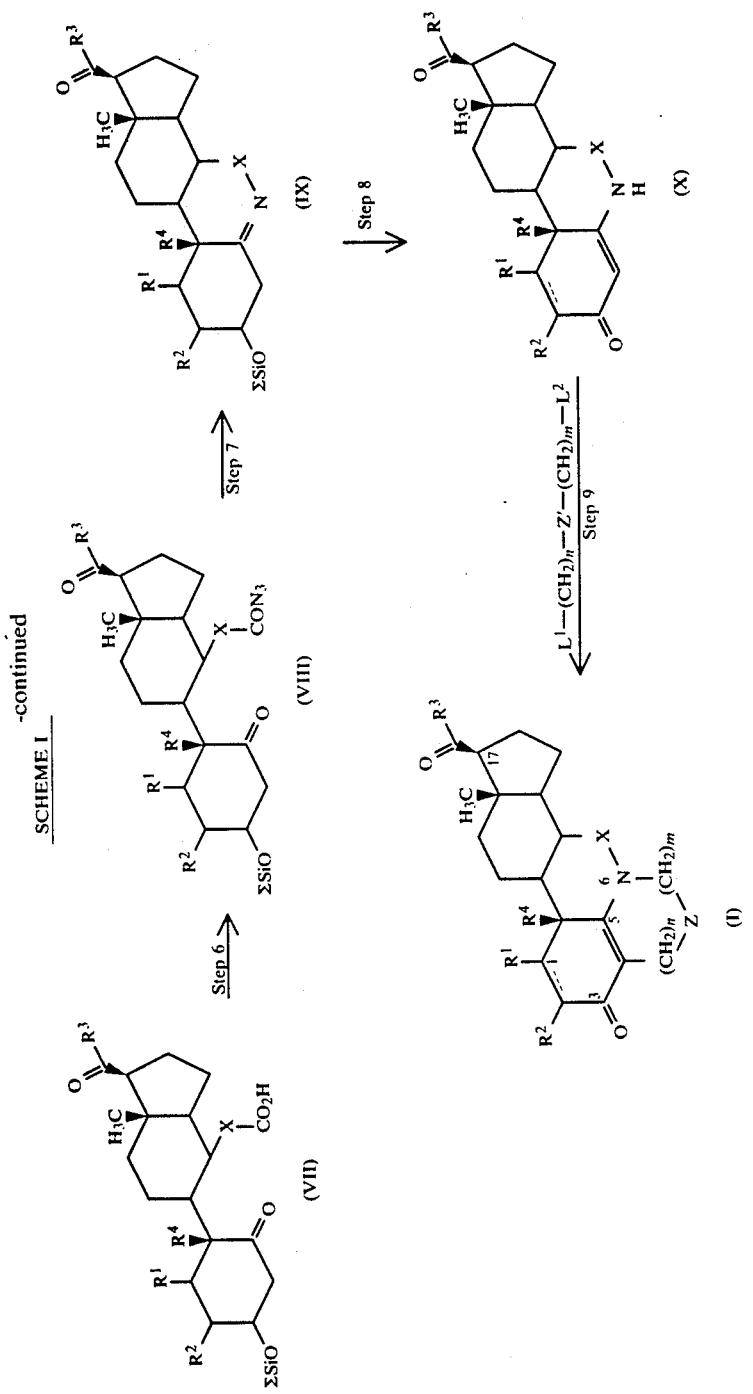

In Step 1 of Scheme I the carboxylic acid group at the 17 position of a compound of formula (II) described in Org. Synth. 5, 8, is converted to the corresponding ketone, ester or amide of compound (III) accompanied by deprotection of the hydroxy group at the 3 position. This may be accomplished by activating the carboxylic acid group toward nucleophilic displacement by treatment with an activating agent such as N,N-bis[2-oxo-3-oxazolidinyl]phosphorinic chloride (BOP-Cl) or conversion to the corresponding acid halide group by treatment with a halogenating agent such as oxalyl chloride or thionyl chloride in an aprotic solvent such methylene chloride at $-5°$ to $10°$ C. The intermediate activated carboxylic acid, e.g., an acid chloride, may be reacted with H—$R^3$ (wherein $R^3$ is as defined for formula (I)) when $R^3$ is an amino group, at room temperature in an aprotic solvent. When $R^3$ is alkyl, alkenyl, lower cycloalkyl, lower alkoxy, or adamantyl, the activated acid is first reacted with an alkyl hydroxyl amine, such as N-methoxy-N-methyl amine and the resulting amide is treated with $R^3M$ (wherein M is a metal, such as magnesium or lithium) in a polar, aprotic solvent such as THF or diethyl ether, at a temperature in the range of about 0 to about $-78°$ C. Alternatively a compound of formula (III) wherein $R^3$ is $OCH_3$ may be prepared from pregnenolone as described by Rasmusson, et al., *J Med. Chem.*, 27, 1690 (1984).

In Step 2, a compound of formula (III) is treated with a trisubstituted silyl halide, such as a trialkylsilyl halide, e.g., triisopropylsilyl chloride, at about $25°$ to $75°$ C. in an aprotic solvent such a dimethylformamide to protect the hydroxy group in the 3-position to yield the corresponding trisubstituted silylated compound of formula (IV).

In Step 3, a compound of formula (IV) is treated with ozone in methanol alone or as a mixture with one or more polar, protic or aprotic solvents, e.g., methylene chloride and methanol, at a temperature substantially below $0°$ C., e.g., from about $-50°$ to about $-80°$ C. to yield a corresponding compound of formula (V).

In Step 4, the compound of formula (V) in methanol alone or as a mixture with one or more polar, protic or aprotic solvents, e.g., methylene chloride and methanol, at about $-20°$ C. is treated with a reductant such as zinc and acetic acid then allowed to slowly warm to room temperature to yield the aldehyde of formula (VI). Alternatively the compound of formula (V) may be taken directly to step 5.

In Step 5, a compound of formula (V or VI) is reacted with an oxidant, such as Jones reagent (see Bowden, et al.*J. Chem. Soc.*, 39 (1946) at about $0°$ C., to yield the corresponding compound of formula (VII).

In Step 6, a compound of formula (VII) is converted to an activated carboxylate derivative such as an acid halide, e.g., chloride, by treatment with a halogenating agent, e.g., oxalyl chloride. The resulting acid halide is reacted with an alkali metal azide, e.g., sodium azide, at about $0°$ to $30°$ C. in an aqueous solvent mixture, such as water and acetone, to yield the corresponding acyl azide compound of formula (VIII). Alternatively, the acid is treated with triphenyl phosphoryl azide in an aprotic solvent such as toluene to yield the acyl azide directly.

In Step 7, an acyl azide compound of formula (VIII) is rearranged with ring closure by warming to reflux in an aprotic solvent, such as toluene, to induce rearrangment to the corresponding isocyanate followed by stirring with a weak acid such as silica gel or by reaction with a strong, sterically hindered base, e.g., potassium t-butoxide, in a protic or aprotic solvent at a temperature in the range of about $90°$ to about $180°$ C., to generate the corresponding compound of formula (IX).

In Step 8, the trisubstituted silyl group of a compound of formula (IX) is converted to the corresponding hydroxy group, i.e., the hydroxy group is deprotected, by reaction with aqueous hydrogen fluoride in a polar solvent at about $0°$ C. to room temperature. Next the hydroxy group is oxidized by reaction with Jones reagent with migration of the double bond to the 4,5 position to generate the corresponding compound of formula (X).

Alternatively the compound of formula (IX) is reacted with reagent to install an election withdrawing protecting group at the 6-nitrogen. For example, (IX) is treated with an acylating agent such as di-t-butyldicarbonate to acylate the 6-nitrogen with migration of the double bond to the 4,5 position or with a sulfonating agent to give a sulfonamide. The trisubstituted silyl protecting group is then removed with a reagent such as tetrabutylammonium fluoride and treated with an oxidant such as pyridinium dichromate to generate the corresponding compound of formula (X) where the 6-nitrogen bears a t-butylcarboxy group. Treatment with an acid, such as trifluoroacetic acid then gives a compound of formula (X).

Optionally, when the 6-nitrogen bears a t-butylcarboxy group, a double bond may then be inserted between the carbon in the 1 position and the carbon in the 2 position by conventional means such as dehydrogenation with 2,3-dichloro-5,6-dicyano-1,4-benzoquinone by refluxing in an aprotic solvent such as dioxane to produce a compound of formula (X) which is unsaturated in the 1,2 position in which the 6-nitrogen bears a t-butylcarboxy. A compound of formula (X) with a double bond in the 1,2 position may then be treated with the anion of trimethylsulfoxonium iodide, prepared by deprotonation with a base such as sodium hydride, in an aprotic, polar solvent such as DMSO to give a compound of formula (X) wherein $R^1$ and $R^2$ taken together form a cyclopropane ring in which the 6-nitrogen bears a t-butylcarboxy group. Removal of the t-butylcarboxy group as described above then gives the corresponding compounds of formula (X).

In Step 9 a compound of formula (X) is treated with a strong base, such as a metal hydride, e.g., sodium hydride, in a polar, aprotic solvent, such as dimethylformamide, then reacted with a compound of formula, $L^1$—$(CH_2)_n$—$Z'$—$(CH_2)_m$—$L^2$, wherein $L^1$ is a leaving group, such as defined in March, J., Advanced Organic Chemistry, 3d. Ed., 179, John Wiley & Sons, New York (1985) and in Hendrickson, J. et al., *Organic Chemistry*, 3d. Ed., 375–377, McGraw Hill, New York (1970), e.g., a halogen atom, and $Z'$ is a group defined as Z in formula (I) or a precursor to such a group, to yield a compound of formula (X) and $L^2$ is a leaving group or a functional group which is readily converted to a leaving group, such as a protected alcohol, substituted in the 4 position with either —$(CH_2)_n$—$Z'$—$(CH_2)_m$—$L^2$ or $L^1$—$(CH_2)_n$—$Z'$—$(CH_2)_m$— depending on the relative ease of displacing $L^1$ and $L^2$. Thus, by judicial choice of $L^1$ and $L^2$ the substitution at the 4 position can be controlled. If $L^2$ is a leaving group, or after conversion of $L^2$ to a leaving group, this intermediate compound is further reacted with an alkali metal iodide, such as sodium iodide in an aprotic solvent such as toluene or dimethylformamide to yield a compound of formula (I).

If Z' is a precursor to a functional group, Z, defined for formula (I), then Z' may be converted to its corresponding functional group.

When the desired compound of formula (I) has n and m as zero and Z is —N=N—, the preferred synthesis is to react a compound of formula (X) with an organic azide, such as an aromatic acid azide, in an aprotic solvent in a temperature range of about 100° to about 180° C. For example, a compound of formula (X) may be reacted with tosylazide in dioxane, in a sealed tube at about 160° C. for about 12 hours.

Further, when the desired compound of formula (I) has n and m as zero and Z is —CH=CH—, the preferred synthesis is to react a compound of formula (X) with a haloacetaldehyde dialkylacetal in an aprotic, polar solvent, such as dimethylformamide at a temperature in the range of about 100 to about 180° C. for several hours. For example, a compound of formula (X) may be reacted with bromoacetaldehyde diethylacetal in dimethylformamide at about 160° C. for 24 hours.

Additionally, a compound of formula (I) wherein $R^3$ is $OR^{11}$ where $R^{11}$ is alkyl, and in particular wherein $R^{11}$ is $CH_3$, may be treated with a strong base, such as lithium hydroxide in a solvent system such as THF or dioxane and water to give a compound of formula (I) compounds of formula (I) wherein $R^3$ is an amino group, alkyl, alkenyl, cycloalkyl or alkoxy.

Optionally, a compound of formula (I) wherein $R^3$ is $OR^9$, and in particular wherein $R^9$ is $CH_3$, may be reduced with a reducing agent such as diisobutyl aluminum hydride and then reoxidized with Collins' reagent ($CrO_3 \cdot 2pyridine$) or another mild oxidant to produce a compound of formula (I) wherein $R^3$ is H, which may be treated with $R^3M$ (wherein M is a metal such as magnesium or lithium) and $R^3$ is alkyl, alkenyl or cycloalkyl to give, after oxidation with pyridinium dichromate, a compound of formula (I) wherein $R^3$ is alkyl, alkenyl or cycloalkyl.

Alternatively, the compounds of formula (I) wherein X is

and both p and q are 1, and $R^5$, $R^6$, $R^7$ and $R^8$ are hydrogen, may be prepared by the procedure shown in Scheme II wherein $R^{1-6}$ are as defined for formula (I):

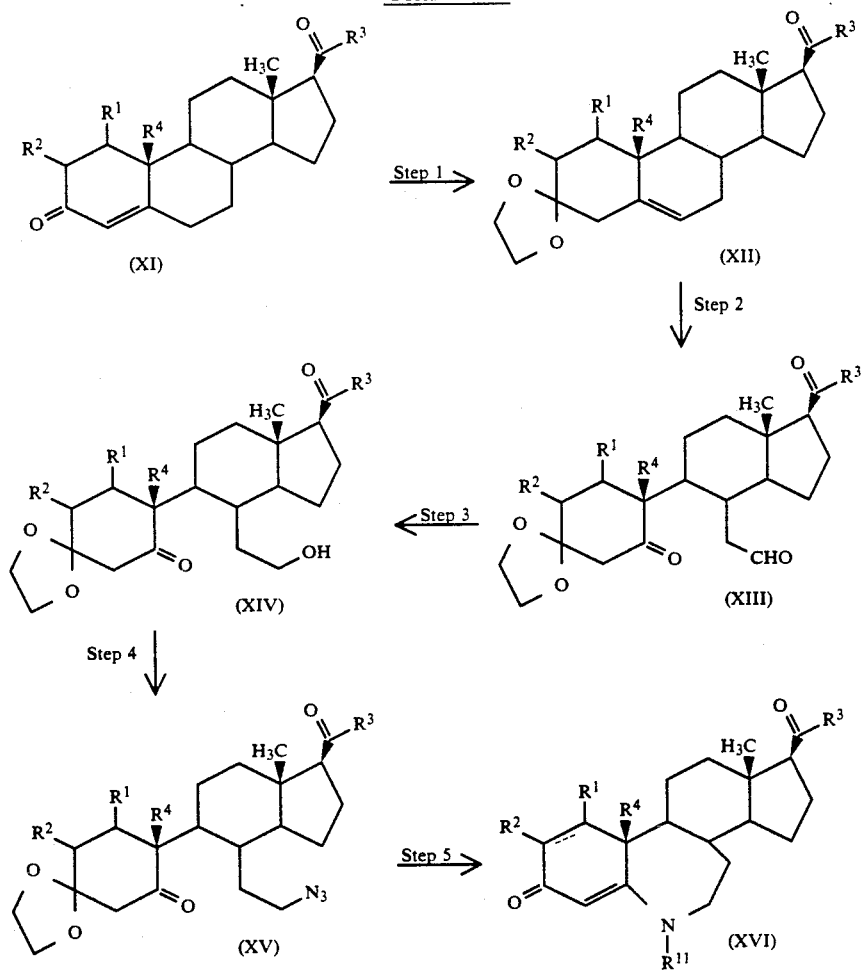

where $R^3$ is OH. An acid of this formula may then be treated as described in Step 1 to yield the corresponding In Step 1 of Scheme II, the enone function of compound (XI) is protected as a ketal with concomitant migration of the double bond to the 5,6 position by refluxing with ethylene glycol in the presence of an acid, such as p-toluenesulfonic acid, in a solvent such as toluene which allows azeotropic removal of water to yield the corresponding compound of formula (XII).

In Step 2, a compound of formula (XII) is treated with ozone in methanol alone or with one or more polar, protic or aprotic solvents mixtures, e.g., methylene chloride and methanol, at a temperature substantially below 0° C. e.g., from about −50° to about −80° C., followed by treatment at about −20° C. with a reductant, such as zinc and acetic acid, then allowed to slowly warm to room temperature to yield the aldehyde of formula (XIII).

In Step 3, a compound of formula (XIII) is reduced with a selective reducing agent, such as lithium tri-t-butoxyaluminumhydride in an aprotic solvent such as THF or diethyl ether to give the corresponding alcohol of formula (XIV).

In Step 4, the alcohol functionality of a compound of formula (XIV) is converted to a leaving group, such as the corresponding methanesulfonate by treatment with methanesulfonyl chloride in an aprotic solvent such as methylene chloride in the presence of a hindered tertiary amine base such as triethylamine. Once transformed to a leaving group, the alcohol is displaced by treatment with a source of azide, such as sodium azide, in a polar, aprotic solvent, such as DMF, to give the corresponding alkyl azide of formula (XV).

In Step 5, a compound of formula (XV) is treated with a reductant such as triphenylphosphine in THF at reflux followed by a strong protic acid such as 4M HCl to give the corresponding compound of formula (XVI), wherein $R^{11}$ is hydrogen.

From a compound of formula (XVI), a corresponding compound of formula (I) where X is $-CH_2CH_2-$ may be prepared by the reactions of Step 9 of Scheme I.

Optionally the compound of formula (XVI) wherein $R^{11}$ is an electron-withdrawing protecting group, e.g. an acyl group, such as t-butylcarboxy, may be treated as described in Step 8 and Step 9 of Scheme I to install the substituents described for $R^1$-$R^3$. The electron-withdrawing protecting groups as $R^{11}$ may be other alkoxycarbonyls (to make a carbomate) or sulfonyls, e.g. $-SO_2$tolyl (to make a sulfonamide).

The compound of formula (I) and the intermediate compounds, (II)–(XVI), shown in Schemes I and II, may be purified by convenient methods of the art, e.g., chromatography, distillation or crystallization.

Steroid 5-α-Reductase In Vitro Assay

Enzyme activity may be determined using microsomes derived from prostate tissue of benign prostatic hypertrophy (BPH) patients or from rat prostate tissue. Prostatic microsomes were prepared by homogenization of the tissue, followed by differential centrifugation of the homogenate. Microsome extracts were incubated with 100 nM [1,2,6,7-$^3$H]-testosterone, 1 mM NADPH and varying amounts of the a compounds of Formula (I), i.e., a test compound, for 60 minutes at 37° C. Corresponding incubations were carried out with no test compound as a control study. The percentage of conversion of testosterone to DHT in the presence of a test compounds compared to the corresponding conversion in the control study was estimated using high pressure liquid chromatography (HPLC) with radiochemical detection. The results of this assay as $IC_{50}$ values for microsomes derived from human prostate tissue are show in Table 1.

TABLE 1

| 5-α-REDUCTASE in vitro INHIBITORY ACTIVITY | |
|---|---|
| Compound/Example | $IC_{50}$ Human |
| 1 | + |
| 2 | ++ |
| 3 | ++ |
| 4 | ++ |

+ = 100–1000 nM
++ = 10–100 nM

In Vivo Evaluation of Steroid 5-α-Reductase Inhibitors

The in vivo activity of steroid 5α-reductase inhibitors may be determined in both acute and chronic rat models. The acute model utilizes castrated male rats which receive testosterone (1 mg) subcutaneously and test compound (10 mg/kg) p.o., at 0.5 hr. and 4.5 hr. prior to sacrifice, respectively. Levels of DHT in the serum and prostate indicate the ability of the test compound to inhibit steroid 5α-reductase in an acute rat model. This activity is compared with that of a known standard, such as MK-906.

The chronic model also utilizes castrated male rats which are dosed daily with testosterone (1 mg) subcutaneously and with test compound (0.01–10 mg/kg) p.o. for 7 days. The animals are then sacrificed and their prostates weighed. Reduction in the size of testosterone-stimulated prostate weight demonstrated activity of the test compound. Known steroid 5α-reductase inhibitors were tested in parallel to ensure consistency of the assay method.

In view of the reported species' differences between human and rat steroid 5α-reductase in vivo, results were tempered by comparison of the in vitro activity against rat and human enzymes. These procedures were supported by pharmacokinetic studies for compounds with predictable reduced efficacy in the rat model.

Utility

The steroid 5α-reductase inhibitors of the present invention are useful in the treatment of androgen responsive diseases, e.g., benign and malignant diseases of the prostate (especially benign prostatic hypertrophy), prostatitis and prostate cancer and androgen mediated diseases of the skin, such as acne, hirsutism and male pattern baldness. For correlation of in vitro, rat in vivo and human clinical data relating to an inhibitor of 5α-reductase, see Stoner, J. Steroid Biochem. Molec. Biol., 37, 375 (1990); Brooks, et al., Steroids, 47, 1 (1986) and Rasmusson, J. Med. Chem., 29, 2298 (1986). Other hormone related diseases, e.g., polycystic ovary disease, would be expected to respond to treatment with these inhibitors.

The amount of compound of formula (I) required to be effective as an 5α-reductase inhibitor will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. However, a suitable effective 5α-reductase inhibitory dose is in the range of about 0.1 to about 50 mg/kg body weight per day, preferably in the range of about 0.5 to about 20 mg/kg per day. The total daily dose may be given as a single dose, multiple doses, e.g., two to six times per day, or by intravenous infusion for a selected duration. Dosages above or below the range cited above are within the scope of the present invention and may be administered to the individual patient if desired and necessary.

For example, for a 75 kg mammal, a dose range would be about 50 to about 1500 mg per day, and a typical dose would be about 200 mg per day. If discrete multiple doses are indicated, treatment might typically be 50 mg of a compound of formula (I) given 4 times per day.

Formulations

Formulations of the present invention for medical use comprise an active compound, i.e., a compound of formula (I), together with an acceptable carrier thereof and optionally other therapeutically active ingredients. The carrier must be pharmaceutically acceptable in the sense of being compatible with the other ingredients of the formulation and not deleterious to the recipient thereof.

The present invention, therefore, further provides a pharmaceutical formulation comprising a compound of formula (I) together with a pharmaceutically acceptable carrier thereof.

The formulations include those suitable for oral, rectal or parenteral (including subcutaneous, intramuscular and intravenous) administration. Preferred are those suitable for oral or parenteral administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into desired unit dosage form.

Formulations of the present invention suitable for oral administration may be presented as discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredient(s) may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a conventional carrier, e.g., cocoa butter or Witepsol S55 (trademark of Dynamite Nobel chemical, Germany) for a suppository base.

Formulations suitable for parenteral administration conveniently comprise a sterile aqueous preparation of the active compound which is preferably isotonic with the blood of the recipient. Such formulations suitably comprise a solution or suspension of a pharmaceutically and pharmacologically acceptable acid addition salt of a compound of the formula (I) that is isotonic with the blood of the recipient. Thus, such formulations may conveniently contain distilled water, 5% dextrose in distilled water or saline and a pharmaceutically and pharmacologically acceptable acid addition salt of a compound of the formula (I) that has an appropriate solubility in these solvents, for example the hydrochloride, isethionate and methanesulfonate salts, preferably the latter. Useful formulations also comprise concentrated solutions or solids containing the compound of formula (I) which upon dilution with an appropriate solvent give a solution suitable for parental administration above.

In addition to the aforementioned ingredients, the formulations of this invention may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

EXAMPLES

The following examples illustrate aspects of this invention but should not be construed as limitations. The symbols and conventions used in these examples are consistent with those used in the contemporary chemical literature, for example, the *Journal of the American Chemical Society*.

EXAMPLE 1

17β-N,N-Diethylcarbamoyl-6-azaandrost-4-en-3-one (Compound 1)

A. 3β-Acetoxyetienic acid diethylamide

To a solution of 3β-acetoxyetienic acid (Org. Syn. 5, 8) (21.46 g, 60 mmol) in methylene chloride (150 mL) under nitrogen is added triethylamine (16.6 mL, 120 mmol), the reaction mixture is stirred for 10 minutes and then cooled to 0° C. Next N,N-bis[2-oxo-3-oxazolidinyl]phosphorodiamidic chloride (BOP-Cl, 15.3 g, 60 mmol) and diethylamine (6.8 mL, 66 mmol) are added and the reaction allowed to warm to room temperature overnight. An aqueous solution of 1N HCl (100 mL) and isopropanol (50 mL) is then added, the mixture stirred 10 min, chloroform is added (500 mL) and the organic layers washed sequentially with 1N HCl, water and saturated aqueous NaCl. The solution is then dried over MgSO$_4$, concentrated to a yellow solid which is dissolved in ethyl acetate (150 mL), boiled with activated charcoal, filtered through silica gel and concentrated to give 3β-acetoxyetienic acid diethylamide as an off-white solid; yield: 16.6 g (67%) of sufficient purity to carry on the following steps.

B. 3β-Hydroxyetionic acid diethylamide

A solution of 3β-acetoxyetienic acid diethylamide (10.03 g, 24 mmol) in anhydrous methanol (250 mL) is treated with anhydrous potassium carbonate (5.0 g) and heated to reflux under nitrogen for 1 hour. The methanol is removed by rotory evaporation, the solid dissolved in ethyl acetate (300 mL), washed sequentially with water and saturated aqueous NaCl then dried over MgSO₄, concentrated and flash chromatographed on silica gel (0 to 20% ethyl acetate to give 3β-hydroxyetionic acid diethylamide as a white solid; yield: 8.95 g (100%)

C. 3β-Triisopropylsilyletienic acid diethl amide

To a solution of 3β-hydroxyetionic acid diethyl amide (8.95 g, 24 mmol) in dimethylformamide (DMF, 25 mL) is added imidazole (4.10 g, 60 mmol) and triisopropylsilylchloride (10.3 mL, 48 mmol) and the reaction heated to 60° C. for about 5 hr. The DMF is then removed by rotary evaporation, diethyl ether added (100 mL), and the solution washed with 1N HCl, saturated aqueous NaCl, dried over MgSO₄ and concentrated by rotary evaporation. The resulting concentrate is flash chromatographed on silica gel (0 to 20% ethyl acetate/hexanes) to give 3β-triisopropylsilyletienic acid diethyl amide as a white foam; yield: 10.28 g (80%).

D. A solution of 3β-Triisopropylsilyletienic acid diethyl amide (10.28 g, 19 mmol), from part C, in methylene chloride (400 mL) and methanol (300 mL) is cooled to −78° C. and treated with ozone until a deep blue color persists. The reaction is then warmed to room temperature, concentrated and flash chromatographed on silica gel (15 to 25% ethyl acetate/hexanes) to give the peroxy compound of formula (V) [wherein $R^1$, $R^2$, $R^4$ and $R^5$ are hydrogen; the bond between the carbons bearing $R^1$ and $R^2$ is a single bond and $R^6$ is diethylamino] as a white foam; yield: 8.70 g (74%); FAB mass spec. MH+ 610.

E. The compound prepared in part D, above, (8.70 g, 14 mmol) is dissolved in acetone and treated with Jones reagent (12 mL, 3.22M, 39 mmol) at 0° C. for 15 min. Next, isopropanol (25 mL) is added, the acetone removed by rotary evaporation, ethyl acetate added (100 mL) and the solution washed with H₂O and saturated aqueous NaCl. The solution is then dried over MgSO₄, concentrated and the residue flash chromatographed on silica gel (15 to 50% ethyl acetate/hexanes) to give the corresponding keto-acid compound of formula (VI) as a white solid; yield 4.09 g (50%); FAB mass spec. MH+ 578.

F. A solution of the keto-acid compound of formula (VI) prepared in part E, above, (3.58 g, 6.2 mmol) in methylene chloride (50 mL) at 0° C. is treated with anhydrous pyridine (1.5 mL) and oxalyl chloride (1.62 mL, 18.6 mmol). After 30 min the reaction is concentrated, eventually at high vacuum and treated with sodium azide (2.0 g, 31 mmol) in H₂O (7 mL). After 30 min the reaction is concentrated, the residue dissolved in ethyl acetate, washed with H₂O, saturated aqueous NaCl, dried over MgSO₄ and concentrated to give corresponding acylazido compound of formula (VII) as a white foam; yield: 3.45 g (92%).

G. 17 β-N,N-Diethylcarbamoyl-3 β-triisopropylsilyloxy-6-azaandrost-2-ene

The acylazido compound of formula (VII) prepared in part F, above, (3.45 g, 5.7 mmol) is dissolved in toluene (40 mL), heated at reflux for 30 min, concentrated, dissolved in t-butanol (100 mL) containing catalytic potassium t-butoxide and heated at reflux for 20 min. After cooling to room temperature, diethyl ether (200 mL) is added, the organics washed with H₂O and saturated aqueous NaCl, the solution dried over MgSO₄, concentrated and flash chromatographed on silica gel (50 to 100% ethyl acetate/hexanes) to give 17 β-N,N-diethylcarbamoyl-3 β-triisopropylsilyloxy-6-azaandrost-2-ene (a compound of formula (VII)) as a light yellow solid; yield: 2.66 g (81%); FAB mass spec. MH+ 531.

H. 17 β-N,N-Diethylcarbamoyl-6-azaandrost-4-en-3-one

A solution of 17 β-N,N-diethylcarbamoyl-3 β-triisopropylsilyloxy-6-azaandrost-2-ene (1.51 g, 2.8 mmol) in acetonitrile (100 mL) at 0° C. is treated with 48% aqueous HF (20 mL), the reaction allowed to warm to room temperature and stirred for 2 hours. The solution is then diluted with methylene chloride (200 mL), washed with H₂O and saturated aqueous bicarbonate, dried over MgSO₄ and concentrated to an off-white solid; yield 1.02 g crude (96%). A solution of this solid (0.48 g, 1.3 mmol) in acetone (100 mmol) is treated with Jones reagent (1 mL, 3.22M, 3.2 mmol) and warmed to room temperature. Next, isopropanol is added (10 mL), the reaction concentrated, the residue dissolved in ethyl acetate (75 mL), washed with saturated aqueous bicarbonate, dried over MgSO₄ and concentrated to give 17 β-N,N-diethylcarbamoyl-6-azaandrost-4-en-3-one as an off-white solid; yield: 0.22 g (46%). This material is then triturated with ether to give 172 mg pure white solid; m.p. 253°–256° C. (dec). Anal. Calcd. for $C_{23}H_{36}N_2O_2$; C, 74.15; H, 9.74; N, 7.52%. Found: C, 73.88; H, 9.77; N, 7.44%.

I. 17 β-N,N-Diethylcarbamoyl-6-azaandrost-4,6-diazo-4-en-3-one

A solution of 17 β-N,N-diethylcarbamoyl-6-azaandrost-4-en-3-one (200 mg, 0.537 mmol) and tosylazide (127 mg, 0.644 mmol) in dioxane (3 mL) is heated to 160° C. in a sealed tube for 12 hours. The reaction is allowed to cool, concentrated, cromatographed (50% ethyl acetate/hexanes) and the resulting solid recrystallized from ethyl acetate/hexane to give 17 β-N,N-diethylcarbamoyl-6-azaandrost-4,6-diazo-4-en-3-one as white crystals; yield: 161 mg (75%); m.p. 248°–249° C. Anal. Calcd. for $C_{23}H_{34}N_4O_2$; C, 69.31; H, 8.60; N, 14.06%. Found: C, 69.10; H, 8.64; N, 14.02

EXAMPLE 2

17 β-N,N-Diethylcarbamoyl-6-azaandrost-4,6-etheno-4-en-3-one (Compound 2)

A solution of 17 β-N,N-diethylcarbamoyl-6-azaandrost-4-en-3-one (373 mg, 1.00 mmol) and bromoacetaldehyde diethylacetal (0.15 mL, 1.0 mmol) in dimethylformamide (2 mL) is heated at 160° C. for 24 hours. The reaction is allowed to cool, ice water added (10 mL), combined extracts dried over Na₂SO₄, filtered through a plug of silica, the silica rinsed with 1:1 methylene chloride/acetonitrile (100 mL) and the filtrates concentrated. Flash chromatography of the residue (30% ethyl acetate/hexanes) gives 17 β-N,N-Diethylcarbamoyl-6-azaandrost-4,6-ethano-4-en-3-one as a light yellow solid; yield: 67 mg (17%); m.p. 108°–112° C. Anal. Calcd. for $C_{25}H_{36}N_2O_2 \cdot \tfrac{3}{4}H_2O$; C, 73.22; H 9.22; N, 6.83. Found: C, 73.24; H, 9.03; N, 6.55.

EXAMPLE 3

17 β-N-t-Butylcarbamoyl-6-azaandrost-4,6-etheno-4-en-3-one (Compound 3)

A. 3β-Triisopropylsilyloxyetienic acid methyl ester

A suspension of 3β-hydroxyetienic acid methyl ester (J. Med. Chem. 27, 1690) (516 g, 1.55 mol) in DMF (800 mL) is heated to 55° C., imidazole (264 g, 3.88 mol) added with vigorous mechanical stirring, followed by dropwise addition of triisopropylsilychloride (360 g, 1.87 mol). The reaction becomes homogeneous after about half of the triisopropylsilylchloride is added and the reaction temperature increases to ca. 70° C. The reaction is complete by TLC (35% ethyl acetate/hexanes) after 1.5 hrs and a thick slurry forms. The reaction is then worked up as in Example 1, part C and crystallized from hexanes/methanol to give 3β-triisopropylsilyloxyetienic acid methyl ester as a white crystalline solid; yield: 667 g (88%); m.p. 124°–125° C. Anal. Calcd. for $C_{30}H_{52}O_3Si$; C, 73.71; H, 10.72. Found: C, 73.79; H, 10.74.

B. A solution of 3β-triisopropylsilyloxyetienic acid methyl ester (166 g, 0.34 mol), from part A, in methylene chloride (2 L) and methanol (800 mL) is cooled to −78° C. and treated with ozone until a blue color persists. The peroxy compound of formula (V) may be isolated as in Example 1, part D and recrystallized from hexanes to give an analytical sample; m.p. 119°–121° C. Anal. Calcd. for $C_{31}H_{56}O_7Si$; C, 65.45; H, 9.92. Found: C, 65.37; H, 9.86. However, more conveniently, the reaction is allowed to warm to −50° C. under a stream of nitrogen, zinc dust added (89 g, 1.36 mol), followed by glacial acetic acid (150 mL). The reaction is then allowed to warm to room temperature with stirring, filtered to remove zinc, the solution washed with water, saturated aqueous NaCl, saturated aqueous NaCl, saturated aqueous bicarbonate, dried over $MgSO_4$ and concentrated by rotary evaporation to give crude keto-aldehyde of formula (VI) as a white foam; yield: 176 g (99%).

C. The compound prepared in part B above (176 g, 0.34 mol) is oxidized with Jones reagent as in Example 1, part E to give the corresponding keto-acid of formula (VII) as an off-white solid; yield: 163 g (89%). Recrystallization from ethyl acetate/hexanes gives a white crystalline solid; m.p. 143°–145° C. Anal. Calcd. for $C_{30}H_{52}O_6Si$; C, 67.12; H, 9.76. Found: C, 67.21; H, 9.80.

D. 17β-Carbomethoxy-3β-triisopropylsilyloxy-6-azaandrost-5-ene

A portion of the keto-acid of formula (VII) prepared above (77 g, 0.14 mol) is converted to the acylazide as in Example 1, part F, and is then dissolved in toluene (500 mL), heated to reflux for 5 minutes, cooled to 50° C. and treated with silica gel (150 g). The reaction is allowed to stir overnight, the silica removed by filtration and washed with 4:1 ethyl acetate/methanol (500 mL) to give 17β-carbomethoxy-3β-triisopropylsilyloxy-6-azaandrost-2-ene (a compound of formula ((IX)) as a white foam; yield: 66 g (94%). Flash chromatography on silica gel (30% ethyl acetate/hexanes) gives an analytical sample as a white foam. Anal. Calcd. for $C_{29}H_{51}NO_3Si$; C, 71.11; H, 10.49; N, 2.86. Found: C, 71.04; H, 10.51; N, 2.80.

E. 17 β-Carbomethoxy-6-t-butylcarboxy-6-azaandrost-4-en-3-one

The crude product from above 17 β-carbomethoxy-3β-triisopropylsilyloxy-6-azaandrost-5-ene (66 g, 0.135 mol) is dissolved in pyridine (500 mL), treated with di-t-butyldicarbonate (150 g, 0.69 mol) and allowed to stir overnight. The pyridine is removed by rotary evaporation and tetrabutylammonium fluoride (500 mL, 1M, 0.5 mol) in tetrahydrofuran (THF) added carefully and the reaction heated to reflux for 5 min. The THF is removed by rotary evaporation, the residue dissolved in ethyl acetate (500 mL), washed cautiously with water, saturated aqueous NaCl, dried with $MgSO_4$ and concentrated. This material is dissolved in DMF (500 mL), is treated with pyridinium dichromate (153 g, 0.41 mol) and allowed to stir overnight. The reaction is poured into water (700 mL) and extracted with ethyl acetate (2×500 mL). The combined extracts are washed with water, 5% aqueous $CuSO_4$, saturated aqueous NaCl, dried over $MgSO_4$, concentrated and flash chromatographed (0–60%, diethyl ether/hexanes) to give 17 β-carbomethoxy-6-t-butylcarboxy-6-azandrost-4-en-3-one as an off-white foam; yield: 37.5 g (64%); FAB mass spec. $MH^+$432.

F. 17 β-Carboxy-6-t-butylcarboxy-6-azaandrost-4-en-3-one

A solution of 17 β-carbomethoxy-6-t-butylcarboxy-6-azaandrost-4-en-3-one (15.4 g, 36 mmol), from part E, in dioxane (150 mL) and water (100 mL) is treated with $LiOH.H_2O$ (3.31 g, 79 mmol) and stirred overnight on a water bath. The reaction is poured into saturated aqueous $NaHSO_4$ (150 mL), extracted with methylene chloride (3×100 mL), extracts washed with saturated aqueous NaCl, dried over $MgSO_4$ and concentrated to a volume of 100 mL. At this point crystals begin to form and 2:1 hexanes/ethyl acetate (50 mL) is added, the mixture triturated, cooled to room temperature and 17 β-carboxy-6-t-butylcarboxy-6-azaandrost-4-en-3-one collected as a fluffy white powder; yield: 9.44 g (63%); m.p. 215°–216° C. Anal. Calcd. for $C_{24}H_{35}NO_5.\frac{1}{4}H_2O$; C, 68.30; H, 8.48; N, 3.32. Found: C, 68.45; H, 8.41; N, 3.28.

The mother liquor is diluted with methylene chloride (100 mL), filtered through silica gel, silica washed with 1:1 diethyl ether/hexanes and the eluant concentrated to give recovered 17 β-carbomethoxy-6-t-butylcarboxy-6-azaandrost-4-en-3-one; yield: 2.63 g (17%). The silica pad is then washed with 1:9 methanol/methylene chloride (250 mL), the eluant concentrated, the resulting solid triturated with 2:1 hexanes/ethyl acetate (50 mL), cooled to 0° C. and 17 β-carbomethoxy-6-t-butylcarboxy-6-azaandrost-4-en-3-one collected as a white powder; yield: 2.25 g (15%). The combined yield based on recovered starting material is 94%.

G. 17 β-N-t-butylcarbamoyl-6-azaandrost-4-en-3-one

A sample of 17 β-N-t-butylcarboxy-6-azaandrost-4-en-3-one (2.03 g, 4.86 mmol), from part F, is coupled with t-butyl amine as described in Example 1, part A, to give crude 17 β-N-t-butylcarboxy-6-azaandrost-4-en-3-one which is dissolved in methylene chloride (30 mL) and treated with trifluoroacetic acid (4 mL) at room temperature. After 3 hrs the reaction is concentrated, methylene chloride (50 mL) and saturated aqueous bicarbonate (50 mL) added, the layers separated, methylene chloride washed with saturated aqueous NaCl, dried over MgSO₄, concentrated and chromatographed on silica gel (0-10% methanol/methylene chloride) to give 17 β-N-t-butylcarbamoyl-6-azaandrost-4-en-3-one as a white solid; yield: 1.04 g (57%). Recrystallization from methylene chloride/hexanes gives an analytical sample as a white crystalline solid; m.p. 186°-189° C. Anal. Calcd. for C₂₃H₃₆N₂O₂·⅜H₂O; C, 72.83; H, 9.77; N, 7.38. Found C, 72.95; H, 9.85; N, 7.22.

H. 17 β-N-t-butylcarbamoyl-6-azaandrost-4,6-etheno-4-en-3-one (Compound 3)

The compound 17 β-N-t-butylcarbamoyl-6-azaandrost-4-en-3-one, described in part G above, is treated according to the procedure described in Example 2 to give 17 β-N-t-butylcarbamoyl-6-azaandrost-4,6-etheno-4-en-3-one as a tan powder. Recrystallization from ethyl acetate/hexanes gives an analytical sample as light tan crystals; m.p. 236°-241° C. Fab mass spec. MH⁺397.

EXAMPLE 4

17β-N-t-Butylcarbamoyl-6-azaandrost-4,6-butano-4-en-3-one (Compound 4)

A solution of 17β-N-t-butylcarbamoyl-6-azaandrost-4-en-3-one (373 mg. 1.00 mmol), in dimethylformamide is treated with sodium hydride (50 mg, 60%, 1.25 mmol) at 0° C. for 30 minutes before the addition of 1,4-dibromobutane (0.179 mL, 1.5 mmol). After 30 minutes further the reaction is poured into ice water and extracted with methylene chloride (3×10 mL), dried over Na₂SO₄, concentrated and filtered through a plug of silica with 1:1 methylene chloride/acetonitrile followed by 10% methanol/methylene chloride. The methanolic fractions are concentrated to give crude 17β-N-t-butylcarbamoyl-6-(4-bromobutyl)-6-azaandrost-4-en-3-one. This material is dissolved in toluene (5 mL) and dimethylformamide (1.5 mL), sodium iodide added and the mixture heated at reflux for 7 hrs. The reaction is cooled, water added, extracted with methylene chloride (3×20 mL), dried over Na₂SO₄, concentrated and chromatographed (50% ethyl acetate/hexane) to give 17β-N-t-butylcarbamoyl-6-azaandrost-4,6-butano-4-en-3-one as a white solid; yield: 150 mg (35%). Recrystallization from ethyl acetate/hexanes gives an analytical sample as white crystals; m.p. 173°-174° C. Anal. Calcd. for C₂₇H₄₂N₂O₂·¼H₂O; C, 75.29; H, 9.94; N, 6.50. Found: C, 75.21; H, 10.04; N, 6.20.

EXAMPLE 5

Pharmaceutical formulations (A) Transdermal System—For 1000 Patches

| Ingredients | Amount |
| --- | --- |
| Active compound | 400 g |
| Silicone fluid | 450 g |
| Colloidal silicone dioxide | 25 g |

The silicone fluid and active compound are mixed together and the colloidal silicone dioxide is added to increase viscosity. The material is then dosed into a subsequently heat sealed polymeric laminate comprised of the following: polyester release liner, skin contact adhesive composed of silicone or acrylic polymers, a control membrane which is a polyolefin (e.g. polyethylene), polyvinyl acetate or polyurethane, and an impermeable backing membrane made of a polyester multilaminate. The resulting laminated sheet is then cut into 10 sq. cm patches.

(B) Oral Tablet—For 1000 Tablets

| Ingredients | Amount |
| --- | --- |
| Active compound | 50 g |
| Starch | 20 g |
| Magnesium Stearate | 1 g |

The active compound and the starch are granulated with water and dried. Magnesium stearate is added to the dried granules and the mixture is thoroughly blended. The blended mixture is compressed into tablets.

(C) Suppository—For 1000 Suppositories

| Ingredients | Amount |
| --- | --- |
| Active compound | 25 g |
| Theobromine sodium salicylate | 250 g |
| Witepsol S55 | 1725 g |

The inactive ingredients are mixed and melted. The active compound is then distributed in the molten mixture, poured into molds and allowed to cool.

(D) Injection—For 1000 Ampules

| Ingredients | Amount |
| --- | --- |
| Active Compound | 5 g |
| Buffering Agents | q.s. |
| Propylene glycol | 400 mg |
| Water for injection | 600 mL |

The active compound and buffering agents are dissolved in the propylene glycol at about 50° C. The water for injection is then added with stirring and the resulting solution is filtered, filled into ampules, sealed and sterilized by autoclaving.

(E) Capsule—For 1000 Capsules

| Ingredients | Amount |
| --- | --- |
| Active Compound | 50 g |
| Lactose | 450 g |
| Magnesium stearate | 5 g |

The finely ground active compound is mixed with the lactose and stearate and packed into gelatin capsules.

We claim:

1. A compound of formula (I):

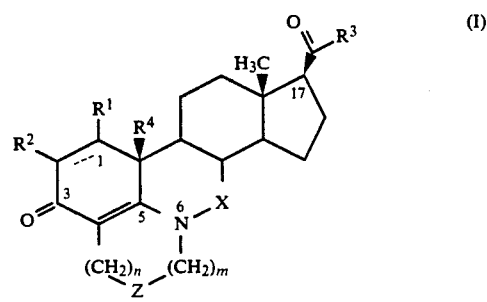

wherein

R¹ and R² are
   i) independently hydrogen or lower alkyl and the bond between the carbons bearing R¹ and R² is a single or a double bond, or
   ii) taken together are a —CH₂— group to form a cyclopropane ring, and the bond between the carbons bearing R¹ and R² is a single bond;

X is CH₂:

R³ is lower alkyl, lower alkenyl, lower cycloalkyl, lower alkoxy, thiopyridyl, adamantyl, —NR⁹R¹⁰ or —Ar—NR⁹R¹⁰
wherein R⁹ and R¹⁰ are
   i) independently, hydrogen or lower alkyl, lower alkenyl, lower alkynyl, lower cycloalkyl, lower alkoxy, phenyl, naphthyl, benzyl, norbornyl or
   ii) taken together with the linking nitrogen to form a 4 to 8 atom heterocyclic group,

wherein:
Y represent), CH₂, —N= NH or N(lower alkyl) optionally substituted with one or more lower alkyl groups;
Ar is phenyl or naphthyl;
R⁴ is hydrogen or methyl;
Z is —CH₂CH₂— or —CH=CH—;
n and m are independently 0, 1 or 2;
and pharmaceutically acceptable salts thereof.

2. A compound of claim 1 which is a compound of formula (IB) or (IC)

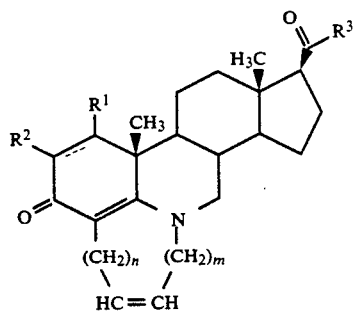

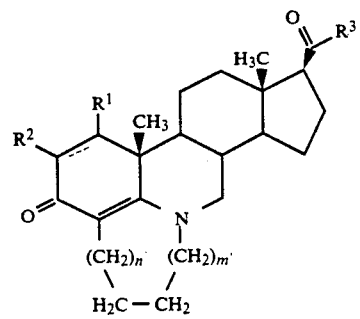

3. The compound of claim 1 which is
17β-N,N-Diethylcarbamoyl-6-azaandrost-4,6-etheno-4-en-3-one,
17β-N-t-butylcarbamoyl-6-azaandrost-4,6-etheno-4en-3-one, or
17β-N-t-butylcarbamoyl-6-azaandrost-4,6-butano-4-en-3-one.

4. A method of inhibiting 5α-testosterone reductase enzyme comprising contacting said enzyme with an effective 5α-testosterone inhibitory amount of a compound of claim 1.

5. A pharmaceutical formulation comprising a compound of claim 1 in a pharmaceutically acceptable carrier thereof.

* * * * *